(12) United States Patent
Li et al.

(10) Patent No.: US 7,910,710 B2
(45) Date of Patent: Mar. 22, 2011

(54) DNA ENZYMES

(75) Inventors: Yingfu Li, Dundas (CA); John Brennan, Dundas (CA); Shirley Mei, Vancouver (CA); Zhongjie Liu, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 849 days.

(21) Appl. No.: 10/504,616

(22) PCT Filed: Feb. 11, 2003

(86) PCT No.: PCT/CA03/00198
§ 371 (c)(1),
(2), (4) Date: Feb. 16, 2005

(87) PCT Pub. No.: WO03/068963
PCT Pub. Date: Aug. 21, 2003

(65) Prior Publication Data
US 2006/0292561 A1    Dec. 28, 2006

Related U.S. Application Data

(60) Provisional application No. 60/356,727, filed on Feb. 15, 2002, provisional application No. 60/402,556, filed on Aug. 12, 2002, provisional application No. 60/431,229, filed on Dec. 6, 2002.

(51) Int. Cl.
*C07H 21/02*    (2006.01)
(52) U.S. Cl. ..................... 536/23.1; 536/23.2; 536/23.4
(58) Field of Classification Search ............... 536/23.1, 536/23.2, 23.4
See application file for complete search history.

(56) References Cited

U.S. PATENT DOCUMENTS 6,706,474 B1 *   3/2004   Lu et al. ........................... 435/6
6,773,885 B1 *   8/2004   Walder et al. .................... 435/6

FOREIGN PATENT DOCUMENTS

WO    WO 96/17086 A1    6/1996
WO    WO 98/27104 A1    6/1998

OTHER PUBLICATIONS

Li et al., A Highly Sensitive and Sective Catalytic DNA Biosensor for Lead Ions, J. Am. Chem. Soc. 2000, 122, pp. 10466-10467.*
Milan N. Stojanovic et al.; Homogeneous assays based on deoxyribozyme catalysis; Nucleic Acids Research; 2000, vol. 28, No. 15; pp. 2915-2918; Oxford University Press.
Alison V. Todd et al.; DzyNA-PCR: Use of DNAzymes to Detect and Quantify Nucleic Acid Sequences in a Real-Time Fluorescent Format; Clinical Chemistry, 2000, vol. 46, No. 5, pp. 625-630; American Association for Clinical Chemistry.
Shirley H. J. Mei et al.; An Efficient RNA-Cleaving DNA Enzyme that Synchronizes Catalysis with Fluorescence Signaling; Journal of the American Chemical Society; Jan. 15, 2003; vol. 125, No. 2, pp. 412-420; Published on the Web Dec. 13, 2002.

* cited by examiner

*Primary Examiner* — Amber D. Steele
(74) *Attorney, Agent, or Firm* — Gowling Lafleur Henderson LLP

(57) ABSTRACT

Methods for the selection of novel signaling allosteric DNA enzymes are provided. In particular, fluorescent signaling allosteric DNA enzymes are described. The selection system is based on the cleavage of an ribonucleotide flanked by a fluorophore modified nucleotide and a quencher modified oligonucleotide. Both cis-acting and trans-acting allosteric DNA enzymes are identified, as well as aptamer/DNA enzyme conjugates.

1 Claim, 9 Drawing Sheets

A

FDNA
5'-GATGTGTCCGTGCFTTTTTCGA

FQDNA
5'-GATGTGTCCGTGCFQTTTTCGA

F1QDNA
5'-GATGTGTCCGTGCFArQTTTCGA

F2QDNA
5'-GATGTGTCCGTGCFArTQTTCGA

F3QDNA
5'-GATGTGTCCGTGCFArTTQTCGA

DNA ENZYMES

The present application claims priority from number PCT/CA03/00198 filed Feb. 11, 2003. The application also claims priority from US provisional applications Nos. 60/356,727 filed Feb. 15, 2002; 60/402,556 filed Aug. 12, 2002; and 60/431,229 filed Dec. 6, 2002.

FIELD OF THE INVENTION

The present invention is directed to methods for the detection and isolation of nucleic acid enzymes which possess desired characteristics. It is also directed to the enzymes isolated according to the methods described and assays based on the use of those enzymes. In particular, it relates to the generation of fluorescent signaling reporters with substrate and/or reaction specificity.

BACKGROUND OF THE INVENTION

Throughout this application, various references are cited in parentheses to describe more fully the state of the art to which this invention pertains. The disclosures of these references are hereby incorporated by reference into the present disclosure, and for convenience the references are listed in the list of references appended hereto.

Over the past decade, there have been significant advances in the development of selective biosensors based on the use of DNA as a biorecognition element. While the majority of DNA based sensors are designed to detect complementary DNA, many recent reports have demonstrated that single-stranded DNA can also form intricate tertiary structures that allow it to selectively bind to non-DNA targets (so called aptamers)[1,2] or perform catalysis of chemical reactions.[3,4] To date, over 100 DNA sequences have been reported for facilitating many types of chemical transformations.[5] In spite of having very limited chemical functionalities, deoxyribozymes that perform catalysis with surprising efficiency have been reported in a number of studies.[6] For example, a small DNA enzyme known as 10-23 performs site-specific RNA cleavage with a very impressive $k_{cat}$ of ~10 $min^{-1}$.[7] It is clear that the lack of a 2_-hydroxyl group in DNA relative to RNA is not a detriment to catalytic performance. Furthermore, the catalytic capabilities of DNA can be enhanced through the use of metal ions[8] and small-molecule cofactors[9] as well as through modification with chemical functionalities that are useful for catalysis.[10] Furthermore, when compared to ribozymes, deoxyribozymes are easier to prepare and more resistant to chemical and enzymatic degradation, and therefore, properly engineered and catalytically efficient DNA enzymes are very desirable elements for the construction of rugged biosensors.

Allosteric ribozymes and deoxyribozymes have tremendous potential for wide-ranging applications in the diagnostic, biosensing and drug screening fields. The use of deoxyribozymes with fast catalytic rates and large turnover numbers allows for the engineering of effective allosteric DNA enzymes for practical applications where rapid enzymatic action is essential. To engineer catalytic DNA probes for detection directed applications, it is very desirable to use DNA enzymes that can couple enzymatic activity with fluorescence signaling capability so that easy and fast detection can be performed in real time without the need for time-consuming separation steps.

SUMMARY OF THE INVENTION

The present invention provides a de novo fluorescence-generating RNA-cleaving DNA enzyme system that maintains low background fluorescence yet is capable of generating a very large fluorescent signal upon RNA cleavage, and which exhibits a very large catalytic rate constant. A method for the detection and isolation of DNA enzymes is provided. The RNA-cleaving DNA enzyme of the present invention uniquely link chemical catalysis with real-time fluorescence signaling capability. Two specific examples of this system, a cis-acting enzyme capable of autocatalysis, and a trans-acting enzyme that acts on a specific chimeric substrate, are provided. Development of an allosteric DNA enzyme controlled by aptamer target binding is also demonstrated. In a preferred embodiment, a known ATP aptamer is conjugated to the cis-acting enzyme.

In one aspect of the invention, there is provided a signaling DNA enzyme construct. The construct comprises a) an enzymatic DNA sequence capable of cleaving at a ribonucleotide site and b) a DNA chain having a ribonucleotide linkage flaked by a fluorophore modified obigonucleotide and a quencher modified obigonucleotide in sufficient proximity to each other whereby, in the absence of catalysis, fluorescence from the fluorophore is quenched by the quencher.

In a preferred embodiment, the enzymatic DNA sequence is a cis-acting enzyme having the sequence defined in SEQ.ID.NO.7 or SEQ. ID. NO.: 8.

In another preferred embodiment, the enzymatic DNA sequence is a trans-acting DNA enzyme having the sequence of SEQ.ID.NO. 9.

In a further aspect of the invention, a signaling DNA enzyme construct comprises an aptamer sequence conjugated to the enzymatic DNA sequence.

In a preferred embodiment, the signaling DNA enzyme/aptamer construct comprises the sequence of SEQ.ID.NO. 10.

In another aspect of the invention, there is provided a method of selecting an RNA-cleaving catalytic DNA molecule. The method comprises the following steps:
1. synthesizing a single-stranded DNA molecule having a ribonucleotide flanked by a fluorophore labeled nucleotide on one side and a quencher modified nucleotide on the other side, and having a random sequence insertion site;
2. inserting random DNA sequences into the insertion site to provide a candidate DNA molecule;
3. incubating the candidate DNA molecule in the presence of a co-factor; and
4. detecting the presence or absence of a fluorescent signal, wherein the signal is generated when cleavage occurs at the ribonucleotide thereby separating the quencher from the fluorophore.

The present invention also provides another method for the selection of an enzymatic DNA sequence. The method comprises the steps of:
providing a library of oligonucleotides comprising random sequences;
ligating the oligonucleotides to an acceptor sequence comprising a ribonucleotide linkage flanked by a fluorophore modified nucleotide and a quencher modified oligonucleotide;
determining whether a fluorescent signal is generated due to cleavage of the ribonucleotide linkage; and
amplifying sequences which were cleaved at the ribonucleotide.

In a further aspect of the invention, there is provided a method for selecting autocatalytic DNA from a random pool of DNA, said method comprising the steps of:
1. providing a pool of single stranded DNA molecules comprising a first predetermined sequence, a random sequence and a second predetermined sequence;

2. ligating said single stranded DNA molecules to an acceptor DNA molecule comprising at least one ribonucleotide flanked by a fluorophore modified oligonulceotide and a quencher modified nucleotide at a ligation junction;
3. isolating a single stranded ligated oligonucleotide;
4. incubating said ligated oligonucleotide in the presence of cofactors;
5. measuring RNA-cleavage activity by PAGE;
6. isolating DNA molecules which had been cleaved at a ribonucleotide.

In a preferred embodiment, the DNA selected by the above described method is subjected to further rounds of selection. This comprises the steps of:
7. a first PCR amplification using a first primer which is complementary to a region of the ligated DNA encompassing the ligation junction and a second primer which is complementary to the second predetermined region;
8. a second PCR amplification using a ribo-terminated third primer to provide a double stranded DNA product having a ribonucleotide at the ligation junction;
9. cleavage of the double stranded DNA product at the ribonucleotide;
10. isolation of single stranded DNA molecules as defined in step 1; and
11. a repeat of steps ii) to x) until a sufficient degree of selection is achieved.

The present invention also provides a method for the selection of an aptamer sequence specific for a desired target. The method comprises conjugating random sequences to a signaling autocatalytic DNA enzyme, incubating the conjugated sequence in the presence of the desired target and determining the fluorescent intensity of the solution. In a preferred embodiment, an assay for the detection of important biological targets is provided.

The present invention also provides a kit for the selection of an enzymatic DNA sequence. In one preferred embodiment the kit comprises a DNA construct comprising a DNA claim with a ribonucleotide linkage flanked by a fluorophore modified nucleotide and a quencher modified oligonucleotide and a sequence adapted for insertion of random oligonucleotides. In another embodiment, kit includes a library DNA adapted for insertion of random or known sequences, an acceptor DNA comprising a ribonucleotide flanked by a fluorophore modified nucleotide and a quencher modified oligonucleotide and primers for PCR amplification of RNA cleaving sequences.

In yet another aspect, a method for the detection of a required factor is provided. The method comprises providing a signaling DNA construct, introducing a sample; and determining whether a signal is generated. In a preferred embodiment a method for the detection of metal ions or small molecules is provided.

BRIEF DESCRIPTION OF THE DRAWINGS

Preferred embodiments of the invention are described below with reference to the drawings, wherein.

DETAILED DESCRIPTION

The present invention is directed to enzymes which cleave a substrate at a defined cleavage site. In particular, DNA-containing molecules capable of functioning as enzymatic reporters and methods for their isolation are provided.

Throughout this specification the terms enzymatic DNA molecule, catalytic DNA, DNA enzyme, DNAzyme and deoxyribozyme are used interchangeably. Enzymatically active portions are also encompassed within the terms. The enzymatic DNA molecules of the present invention may be modified by mutations, deletions and/or additions and they may comprise nucleotide analogs. The enzymatic DNA molecules of the present invention cleave an oligonucleotide substrate. Both cis-acting and trans-acting enzymes are encompassed.

Catalytic DNA molecules cleave phosphodiester bonds and thus have many uses both in pharmaceutical/medical applications and in everyday life.

The present invention provides a rapid fluorescence based system for the detection of catalytic DNA molecules that can cleave RNA. A signaling oligonucleotide is synthesized which includes a ribonucleotide. A fluorophore-modified nucleotide is located on one side (e.g. upstream) of the ribonucleotide and a quencher-modified nucleotide is located on the other side (e.g. downstream). It is clearly apparent that the opposite orientation (i.e. the fluorophore-modified nucleotide located downstream of the ribonucleotide and the quencher-modified nucleotide upstream) would also be functional. The quencher-modified nucleotide should be sufficiently close to the fluorophore-modified nucleotide to provide a low background of fluorescence. The signaling oligonucleotide is coupled to random sequences. If the random sequence comprises a DNA enzyme capable of cleaving the signaling oligonucleotide at the ribonucleotide, the fluorophore and the quencher become separated and a significant increase in the fluorescent signal can be detected.

Figure 1:
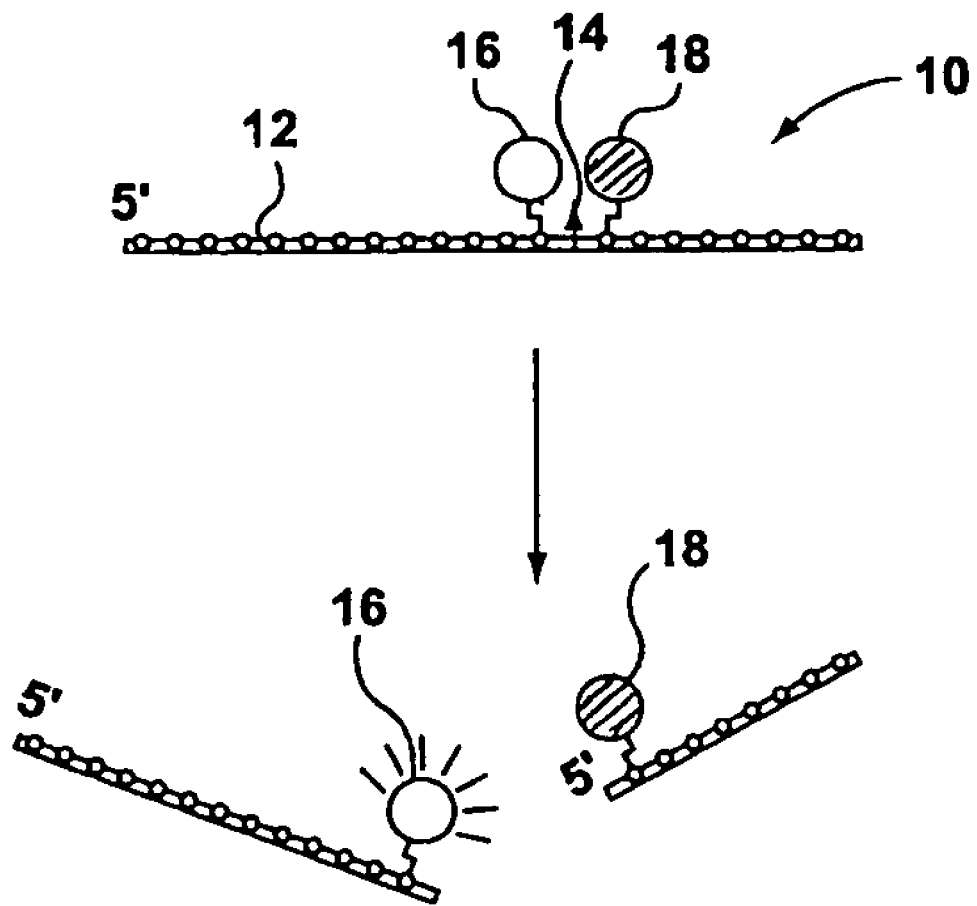
FIG. 1 is a schematic representation of the signal generated upon cleavage of a DNA chain at a ribonucleotide linkage.

The present invention allows for the selection and isolation of a DNA enzyme based on the generation of fluorescent signal. In one aspect of the invention, a signaling DNA enzyme reporter system based on RNA cleavage is provided. The general concept is illustrated in FIG. 1. A reporter 10 is provided which comprises a DNA chain 12 having an RNA linkage 14 embedded therein. A fluorophore 16 is linked to the chain 12 on one side of the RNA linkage and a quencher 18 is linked to the chain on the other side of the RNA linkage. The fluorophore and the quencher are sufficiently close to each other to provide efficient quenching of the fluorescence from the fluorophore by the quencher. This also minimizes false positives. When the RNA linkage is cleaved, the fluorophore and the quencher separate and a fluorescent signal is generated. This system can be used to detect the presence of any moiety that cleaves RNA. This system can also be used to detect the presence of co-factors required by an RNA-cleaving enzyme.

Figure 2:
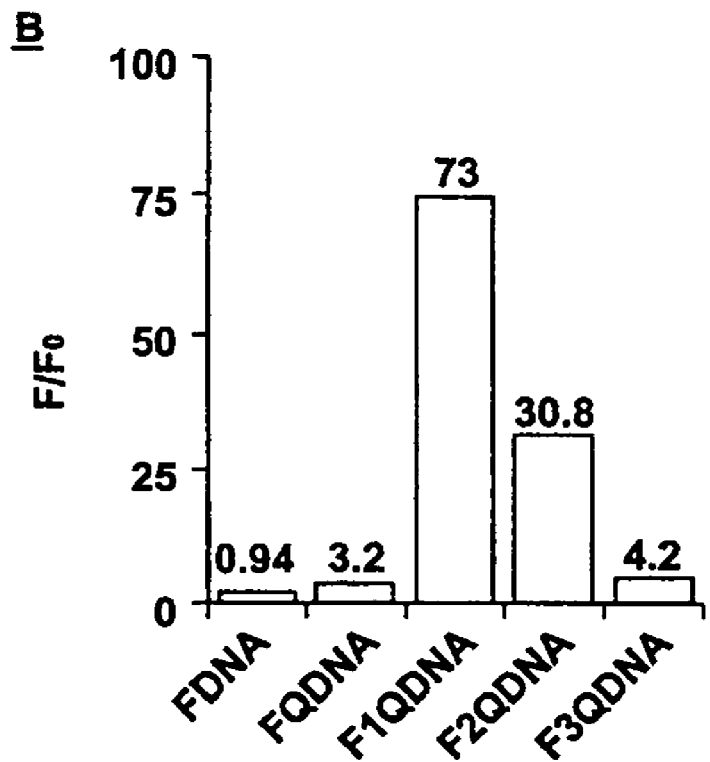
FIG. 2 illustrates the selection of a signaling sequence based on distance between a fluorophore and a quencher wherein from top to bottom the sequences comprise SEQ ID NO: 12, SEQ ID NO: 13, SEQ ID NO: 1, SEQ ID NO: 14, and SEQ ID NO: 15.

An optimal signaling DNA reporter will have a good signal to noise ratio. There is low background in the absence of any enzymatic activity and a strong signal is generated when cleavage has occurred. The effect of the distance between the fluorophore and the quencher on these properties can be assessed using constructs similar to those shown in FIG. 2 and discussed further in Example 2. A series of constructs where the fluorophore and quencher were spaced at different distances were prepared. These constructs comprise, from top to bottom in FIG. 2, SEQ ID NOS: 12, 13, 1, 14, 15. It is well known that RNA can be fragmented with base and NaOH is known to break down RNA and not DNA. Thus, NaOH can be added to the constructs and the fold change in fluorescence can be determined. In this manner a signaling reporter based on cleavage at a particular site can be prepared. Generally, the fluorophore and quencher should be sufficiently close to give a low background in the absence of cleavage and provide a good signal to noise ratio.

In another aspect, the present invention provides a method for the selection and isolation of fluorescent signaling RNA-cleaving autocatalytic DNA molecules. Basically, a DNA construct is provided which includes a ribonucleotide flanked by a fluorophore modified oligonucleotide and a quencher-modified oligonucleofide. The construct also includes a site for insertion of random nucleotide sequences. If the inserted sequence has RNA cleaving activity, the ribonucleotide linkage is cleaved and the fluorophore is separated from the quencher and a fluorescent signal is generated.

Several rounds of selection are preferably done to enrich for the catalytic sequence. In a preferred embodiment a selection scheme similar to the one shown in FIG. 3A and discussed in Example 5 is used to enrich and select the RNA cleaving DNA enzyme.

The selection scheme of the present invention comprises generating a pool of single stranded DNA molecules comprising a random sequence flanked by a predetermined 5' sequence and a predetermined 3' sequence. These DNA molecules are referred to as "library" DNA (SEQ ID NO: 2). An oligonucleotide, referred to herein as an "acceptor"oligonucleotide (SEQ ID NO: 1), comprises a fluorophore modified nucleotide, a quencher modified nucleotide and a ribonucleotide linkage positioned between the fluorophore and the quencher. Another oligonucleotide, termed "template" DNA (SEQ ID NO: 3) is also provided. Template DNA comprises a first sequence which is at least partially complementary to the sequence of the acceptor oligonucleotide and a second sequence which is at least partially complementary to the predetermined 5' sequence of the library DNA. Due to the complementarity of the sequences, the template DNA forms a duplex structure with the acceptor oligonucleotide and the library DNA and brings them into proximity. When a ligase is introduced, the library DNA is ligated to the acceptor oligonucleotide to form a ligated molecule. The duplex structure is dissociated and the ligated molecule can be separated from the template DNA by PAGE.

A particular feature of present invention is that it permits selection and isolation of an enzyme on the basis of fluorescent signaling. It is clearly apparent that the selection scheme of the present invention is not limited to the particular sequences shown in FIG. 3. The general scheme can be used to select a variety of DNA enzymes having different characteristics.

Enzymatic DNA molecules that require the presence of co-factors such as small molecules, peptides, metal ions, metabolites, sugars, nucleic acids, etc. are selected by incubating the ligated molecule in the presence of that factor. If the ligated molecule comprises a DNA enzyme that is responsive to that factor, cleavage will occur at the ribonucleotide linkage. This will result in the generation of a fluorescent signal as the fluorophore and quencher become separated. An example of this is shown in step III of FIG. 3 when metal ions are introduced.

The autocatalytic molecules can then be enriched through a series of polymerase chain reactions. Since the autocatalytic DNA will have the predetermined 3' sequence of the library DNA, a primer complementary to that sequence can be used. This primer is termed P1 (SEQ ID NO: 4). A second primer, P2 (SEQ ID NO:5), comprises a sequence complementary to the acceptor oligonucleotide and the conserved 5' sequence of the pool DNA. PCR with these primers will generate DNA molecules having the sequence of the ligated DNA with the exception of the ribonucleotide. The ribonucleotide is then introduced using a third primer, P3(SEQ ID NO: 6), which is ribo-terminated. After amplification, the DNA is treated with an RNA cleaving moiety, such as NaOH. The cleaved DNA is subjected to PAGE purification and DNA phosphorylation. The 5' phosphorylated DNA is used to initiate a further round of selection. Using this strategy highly selective reporters can even be regenerated in situ.

Figure 3:
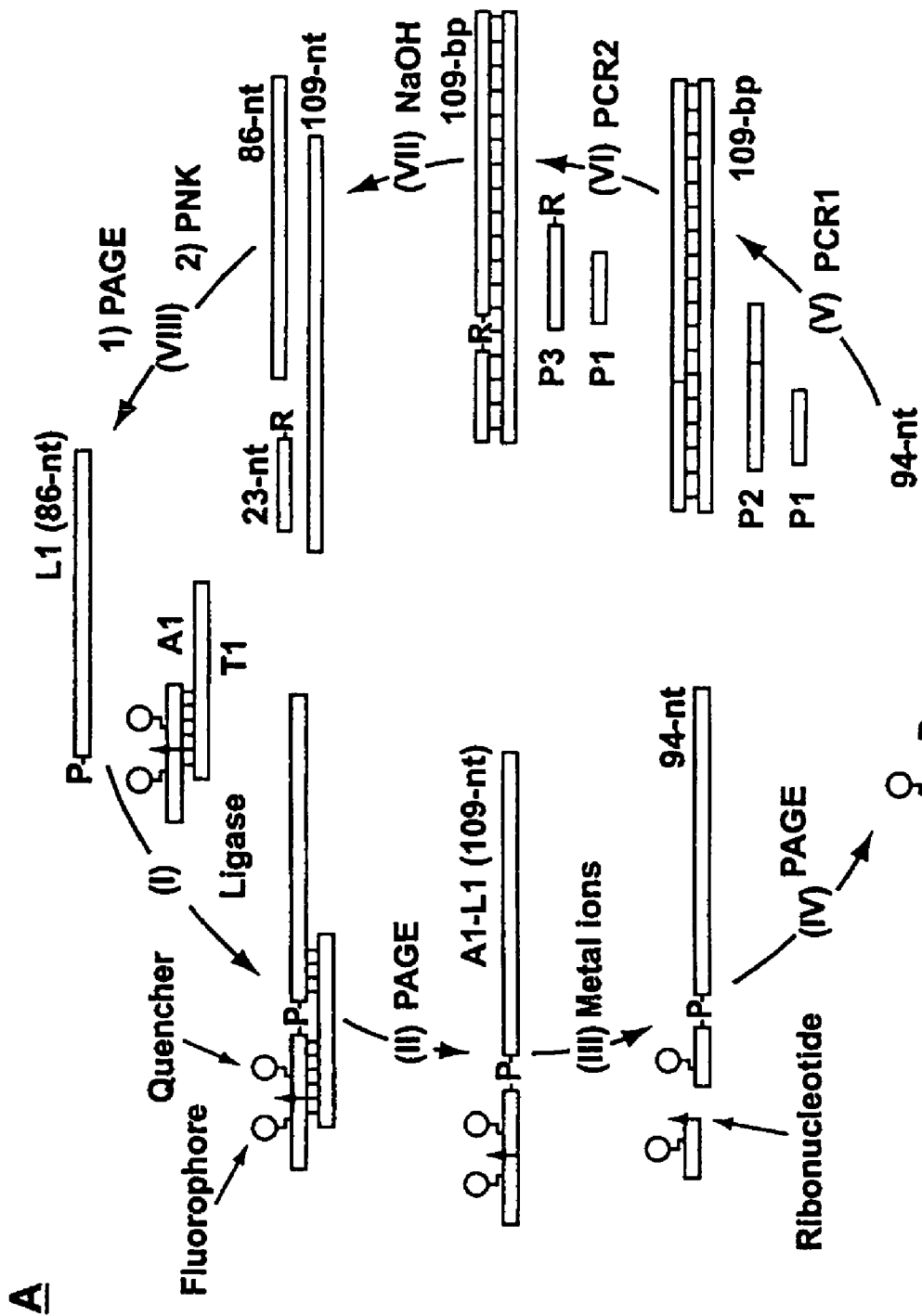
FIG. 3A is a schematic representation of a method for the selection of an RNA-cleaving DNA enzyme.
FIG. 3B illustrates exemplary sequences used to select a DNA enzyme according to the method illustrated in FIG. 3A wherein the Acceptor sequence comprises SEQ ID NO: 1, the Library sequence comprises SEQ ID NO: 2, the template sequence comprises SEQ ID NO: 3, Primer P1 comprises SEQ ID NO: 4, Primer P2 comprises SEQ ID NO: 5, and Primer P3 comprises SEQ ID NO: 6.
FIG. 3C illustrates graphically the enzymatic activity under various selection conditions.
Figure 3:
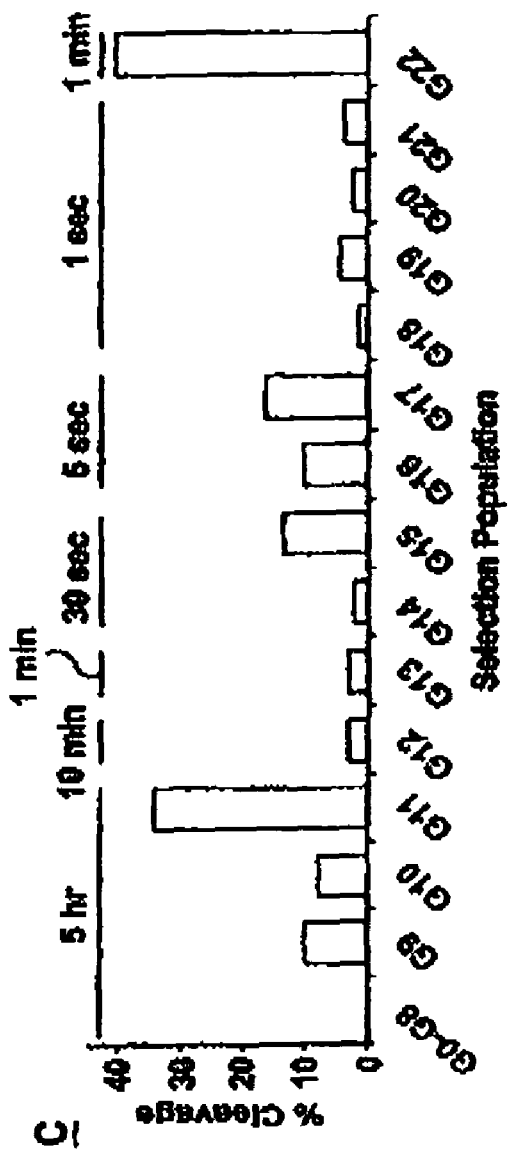

It is clearly apparent to one skilled in the art that the method is generally applicable and is not limited to the specific nucleotide sequences shown in FIG. 3.

The DNA enzyme can be initially selected and enriched by going through a number of selection rounds. In addition, the time allowed for the self cleavage reaction can be gradually decreased to select for the most efficient DNA enzymes as shown in FIG. 3C and discussed further in Example 5. In a preferred embodiment, the techniques will result in clones comprising a single class of DNA enzyme after several rounds of selection.

Figure 4:
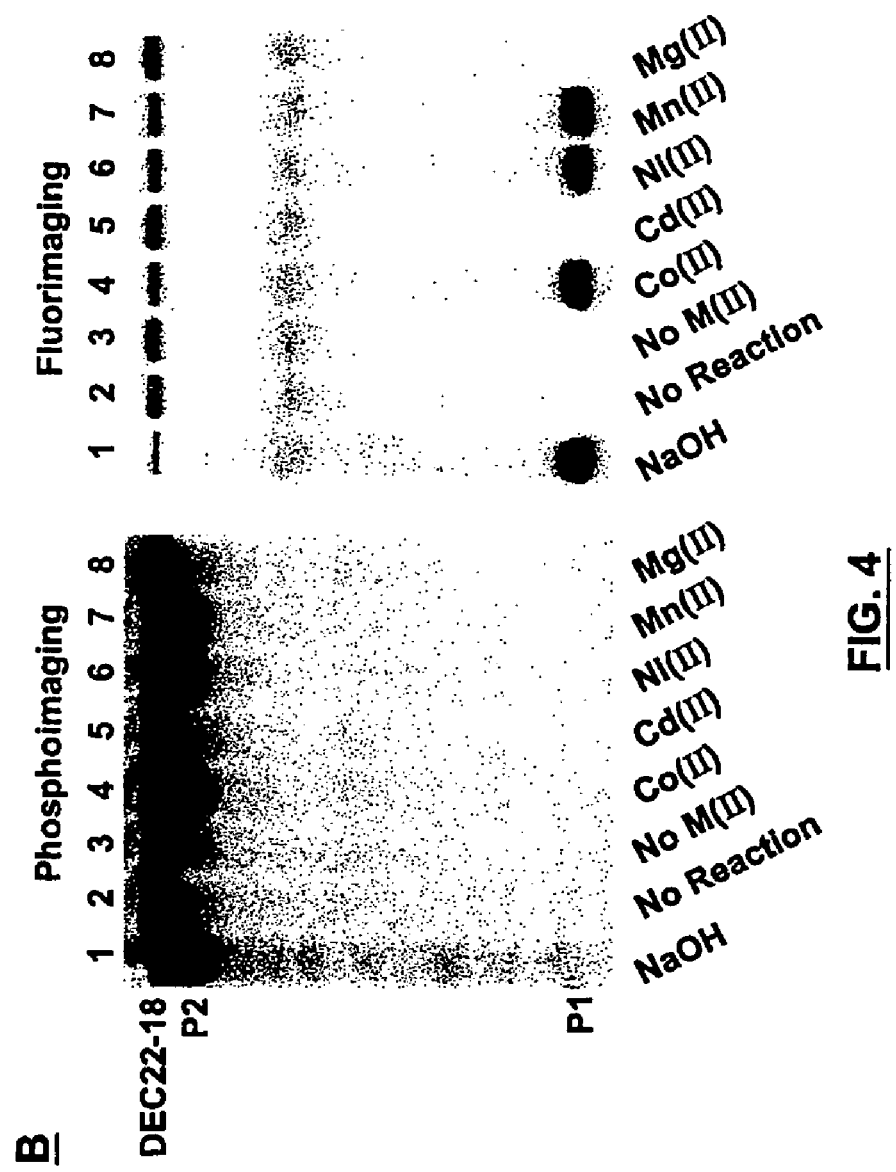
FIG. 4A illustrates the sequence of a cis-acting DNA enzyme construct comprising SEQ ID NO: 7.
FIG. 4B illustrates the signaling properties of the enzyme illustrated in FIG. 4A.

An RNA-cleaving DNA enzyme was isolated using the above-described methodology and was termed DEC22-18. The terminology is based on DNA enzyme, cis-acting, 22 rounds of selection, clone 18. DEC22-18 is a large DNA molecule consisting of 109 nucleotides. The sequence of this enzyme is shown in FIG. 4A and in SEQ ID NO: 7. The catalytic activity of this molecule was confirmed as illustrated in FIG. 4B and described further in Example 7.

Figure 5:
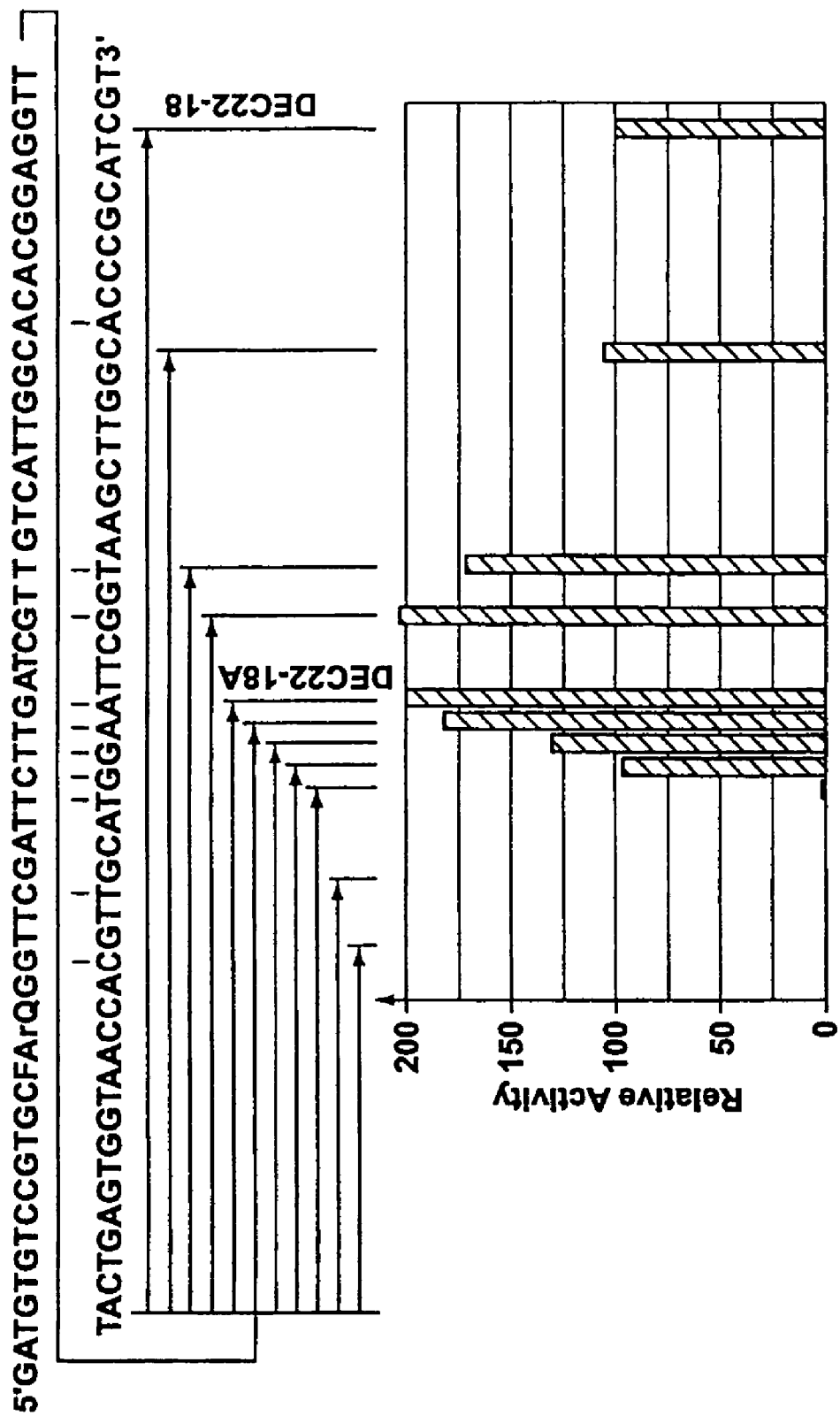
FIG. 5 illustrates the effect of 3' truncations of SEQ ID NO: 7 on signaling activity.

In an aspect of the invention, the minimal sequence required for catalytic activity is determined by doing a series of nucleotide truncations and measuring the enzymatic activity of the truncated molecules. In an exemplary embodiment of the present invention, DEC22-18 was subjected to a series of 3=truncations. The truncation experiments are illustrated in FIG. 5 and described more fully in Example 8. The truncation of the last 26 nucleotides resulted in an enzyme termed DEC18-22A which is a highly efficient enzyme. Once a primary oligonucleotide structure is known, the secondary structure can be predicted using various algorithms. The secondary structure of DEC22-18A was predicted using the M-Fold program and is shown in FIG. 6A.

Figure 6:
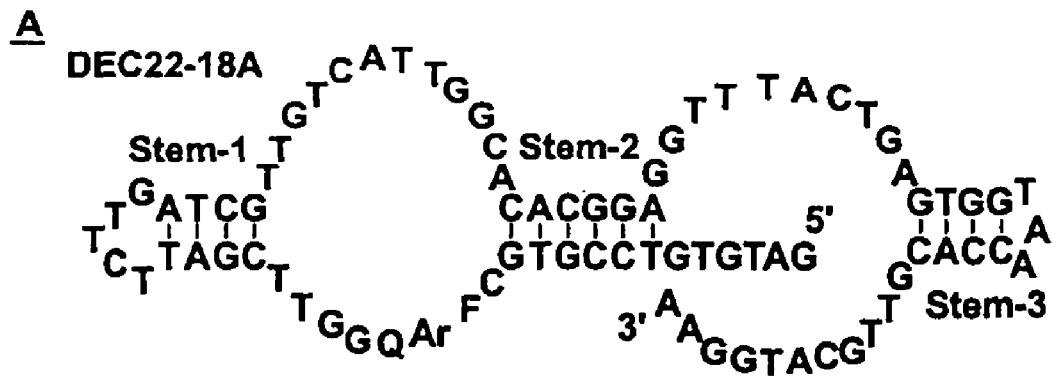
FIG. 6A illustrates the secondary structure of the cis-acting DNA enzyme construct, DEC22-18A comprising SEQ ID NO: 8.
FIG. 6B illustrates the proposed secondary structure of a trans-acting DNA enzyme construct, DET22-18 which comprises SEQ ID NO: 9 and SEQ ID NO: 11.
FIG. 6C is a graphical representation of the kinetic analysis of DET22-18.
Figure 6:
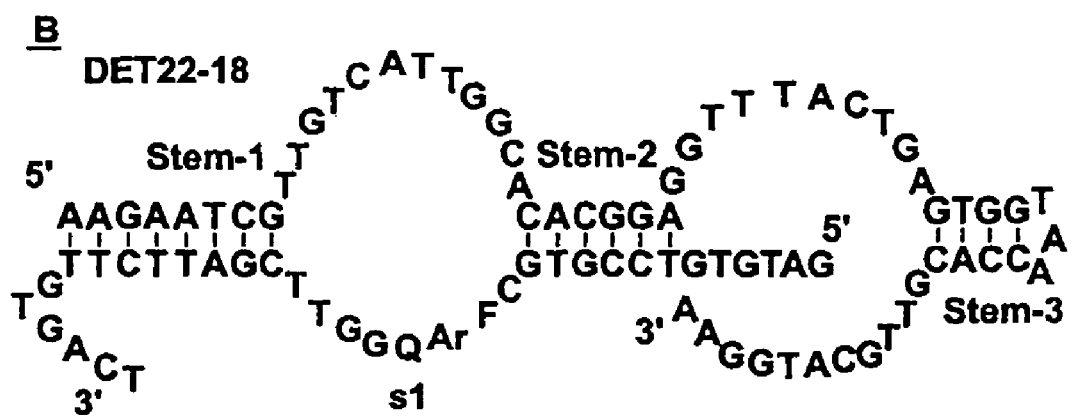
Figure 6:
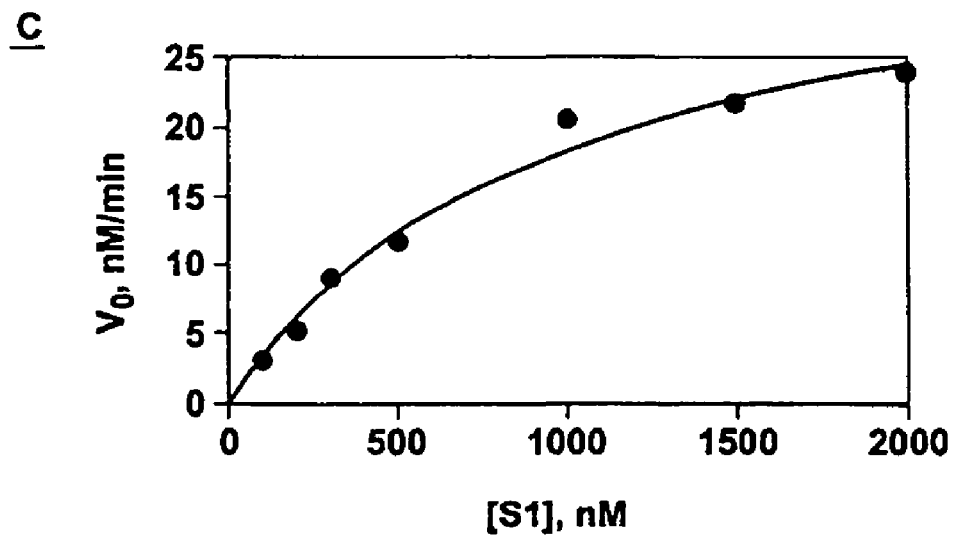
Figure 7:
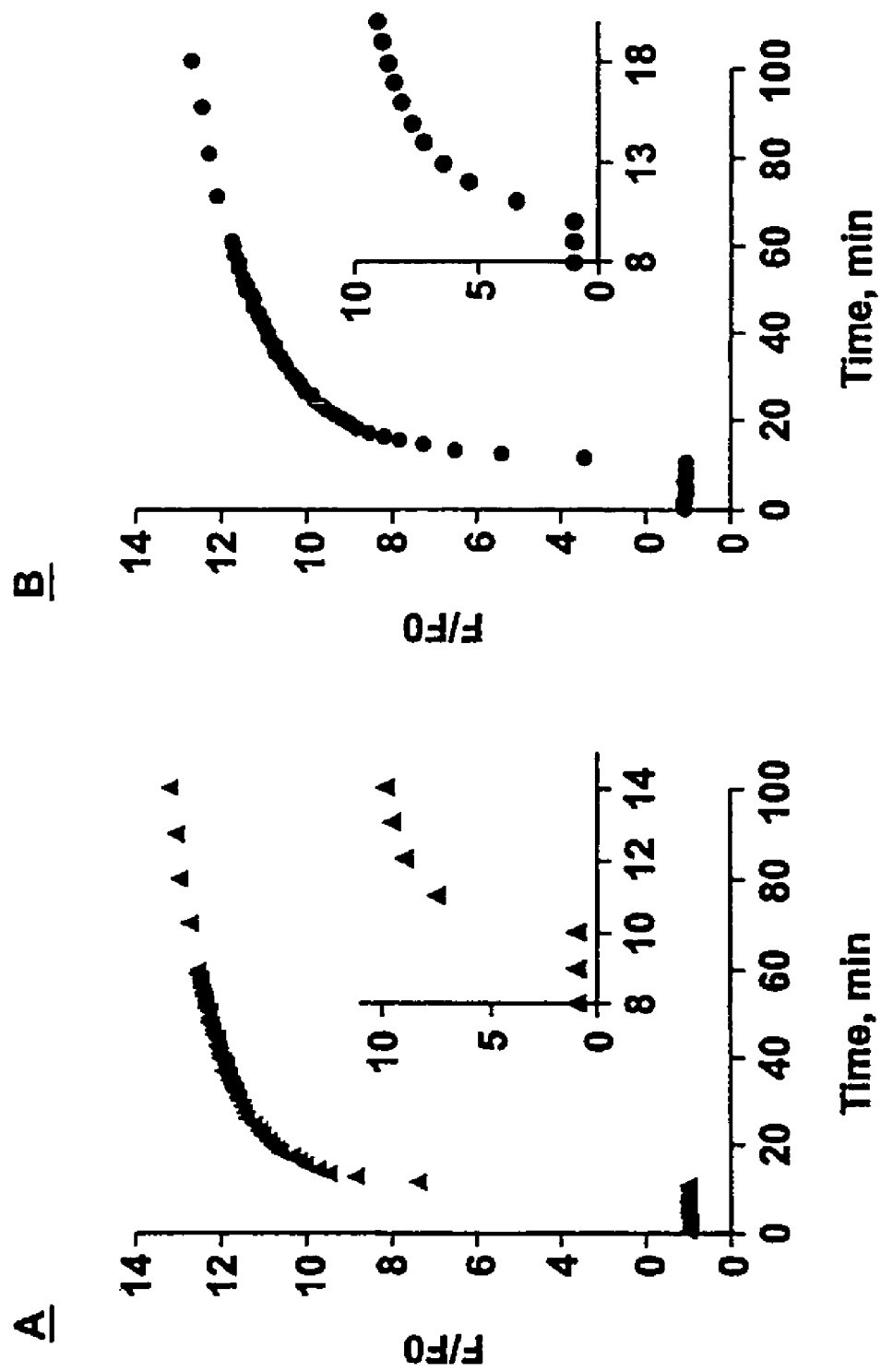
FIG. 7A demonstrates the real-time signaling capability of DET22-18 when the enzyme is in excess.
FIG. 7B demonstrates the real-time signaling capability of DET22-18 when the substrate is in excess.

DEC22-18A is a cis-acting enzyme. Based on the secondary structure of DEC22-18A, it is possible to design a trans-acting DNA enzyme system. A trans-acting DNA enzyme, DET22-18, is also provided. The structure of DET22-18 (SEQ ID NO: 9) and its substrate (SEQ ID NO: 11) are shown in FIG. 6. signaling properties are illustrated in FIGS. 6 and 7 and described more fully in Examples 9 and 10.

Figure 8:
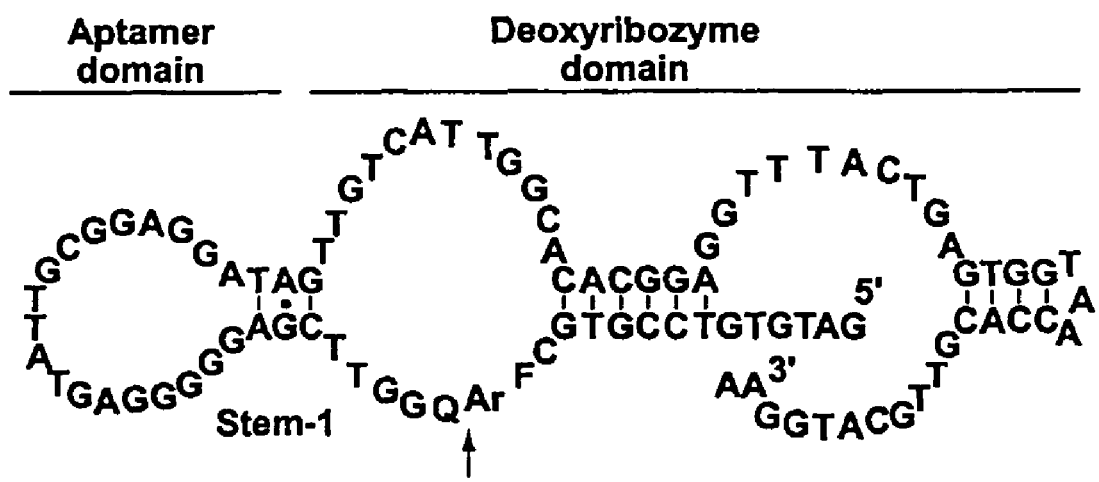
FIG. 8A illustrates an allosteric DNA enzyme contruct comprising SEQ ID NO: 10 where an aptamer sequence is coupled to a signaling DNA enzyme.
FIG. 8B illustrates graphically an activation assay based on introduction of the aptamer target.
FIG. 8C demonstrates the target specificity of the signaling construct.
Figure 8:
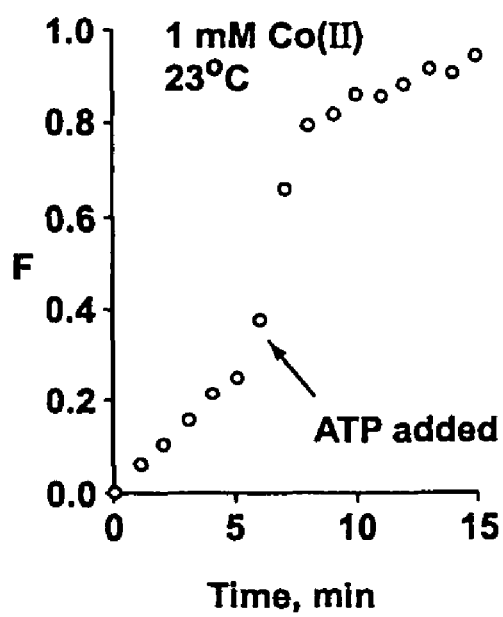
Figure 8:
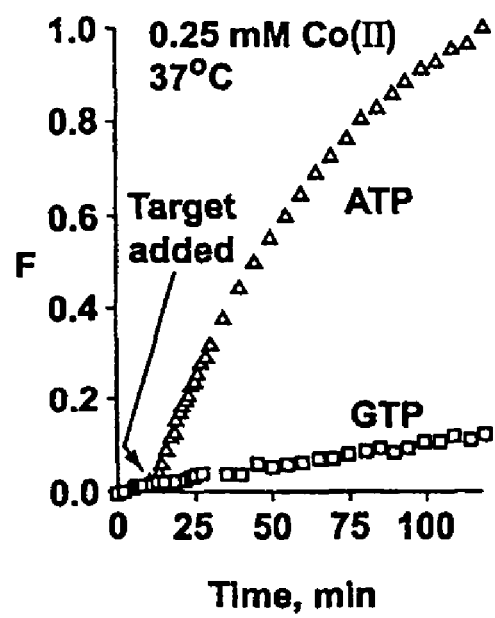

The RNA-cleaving DNA enzymes of the present invention can also be used to design a signaling allosteric deoxyribozyme. An aptamer sequence is conjugated to a DNA enzyme having a stem-loop secondary structure. An exemplary signaling allosteric deoxyribozyme (SEQ ID NO: 10) is shown in FIG. 8 and discussed further in Example 11. In a preferred embodiment, a weak stem is used to conjugate the aptamer sequence to the enzyme sequence. In the absence of the aptamer target, the stem is weak and so the catalytic activity is weak. In the presence of the target, the formation of the stem is promoted and there is a concomitant increase in catalytic activity due to the formation of the secondary structure. The DNA enzyme moiety is modified as described above to include a ribonucleotide flanked by a fluorophore and a quencher. In the absence of aptamer target, the stem formation is weak and there is little or no cleavage at the ribonucleotide. Thus, in the absence of target, the Fluorophore and quencher remain in close proximity and the fluorescence is quenched. In the presence of the aptamer target, the DNA enzyme assumes its secondary structure and cleavage occurs at the ribonucleotide resulting in a fluorescent signal being generated. Thus, the signaling, allosteric DNA enzyme or "aptazyme" can be used to detect the presence of a target molecule.

It is clearly apparent that the signaling DNA enzymes of the present invention can be conjugated to various aptamer sequences using a variety of techniques. Based on the ease with which cleavage can be detected by a fluorescent signal, the signaling enzymes of the present invention can be used to identify aptamer sequences. Random sequences can be conjugated to the deoxyribozyme domain and tested for their ability to bind to various targets.

In a preferred embodiment, a signaling allosteric DNA enzyme comprising DE22-18A conjugated to an aptamer sequence is provided. In a preferred embodiment a signaling allosteric DNA enzyme comprising DE22-18A conjugated to an ATP binding aptamer is provided. The secondary structure of this conjugated DNA molecule is shown in FIG. 8A and the sequence is described in SEQ ID NO: 10. The target reporting capabilities of this molecules are illustrated in FIG. 8B and 8C and discussed further in Example 11. It is clearly apparent the ATP aptamer/DEC22-18 aptazyme detects the presence of ATP and that the signal generated in target specific. Signaling allosteric DNA enzymes incorporating other aptamer sequences are encompassed within the invention.

The signaling DNA enzymes of the present invention are useful in a variety of ways. The signaling DNA enzyme systems of the present invention are well-suited for solution-based assays for detecting specific analytes. Such an assay is easy to use and the detection is extremely rapid since there is no need to have a separation step or to add fluorogenic reagents. The present invention also has the advantage that because selection is done with the fluorophore and quencher in position, the risk of altering the activity of the catalytic DNA by post-labeling reactions is eliminated.

The DNA molecules of the present invention can also be immobilized onto a variety of surfaces, including quartz, glass, silica, various metals and any polymers. The DNA can be immobilized onto optical fibers, planar waveguides or microscope slides. The DNA can be applied as a monolayer or multilayer or it can be entrapped in a polymer solution.

Throughout this description, the use of fluorescein as the fluorophore and DABCYL as the quencher has been described. It is clearly apparent that alternative probe systems that have as effective or enhanced photostability and better scatter rejection can be used. For example, very long life-time probes based on Eu(III) and Tb(III), Ru(II) probes and long-wavelength probes such as Texas Red can also be used. In addition, FRET acceptors and FRET donors can be used to generate a measurable fluorescent signal. The system of the present invention is also well suited of the construction of wave-length shifting fluorescent reporters.

The present invention also provides a kit for the selection of an enzymatic DNA sequence. In one preferred embodiment the kit comprises a DNA construct comprising a DNA claim with a ribonucleotide linkage flanked by a fluorophore modified nucleotide and a quencher modified oligonucleotide and a sequence adapted for insertion of random oligonucleotides. In another embodiment, kit includes a library DNA adapted for insertion of random or known sequences, an acceptor DNA comprising a ribonucleotide flanked by a fluorophore modified nucleotide and a quencher modified oligonucleotide and primers for PCR amplification of RNA cleaving sequences.

The present invention provides signaling allosteric DNA enzymes and methods for their detection, selection and amplification. Both a cis-acting RNA-cleaving DNA enzyme, DEC22-18, and a related trans-acting DNA enzyme, DET22-18, that have uniquely synchronized chemical catalysis/real-time signaling capabilities are provided. DEC22-18 has a unique structural feature wherein the enzyme and substrate are present within the same molecule, leading to an autocatalytic system capable of generating a large fluorescence signal with appropriate divalent metal ions. An advantage of such a system is that since both the catalytic and signaling components are present in a single molecule, Areagentless≡ sensors can be developed based on immobilization of the DNAzyme onto a suitable surface such as that of an optical fiber. In this case, only the presence of the appropriate target would be required to generate a signal. Given the large $k_{obs}$ value and the potential to achieve very significant enhancement in fluorescence intensity from this system, rapid and sensitive detection of target molecules can be achieved with such a reporter.

The trans-acting DNAzyme DET22-18 is a true enzyme with a $k_{cat}$ of ~7 min$^{-1}$, making it one of the fastest DNA enzyme reported to date. The 58-nt DNA enzyme cleaves a chimeric RNA/DNA substrate at the lone RNA linkage surrounded by a closely spaced fluorophore-quencher pair. This unique structure permits the synchronization of chemical cleavage with fluorescence signaling. The extremely short distance between F and Q gives rise to the maximal fluorescence quenching in the starting substrate (for both cis and trans reactions) and results in a very large fluorescence enhancement upon chemical catalysis. At the same time, the covalent integration of F and Q within the same substrate prohibits undesirable long-range movement of the fluorophore and the quencher away from each other so that the potential for false signaling that does not originate from chemical catalysis can be minimized. The signaling DNA enzymes of the present invention have the ability for fast chemical action, synchronized catalysis-signaling capability, excellent fluorescence signaling properties (low background fluorescence, large signal enhancement, and minimal potential for false signaling), and a simple stem-loop structure. This makes them ideal DNA enzymes for engineering useful allosteric deoxyribozyme biosensors with exceptional real-time detection sensitivity and accuracy. A large number of similar DNA enzymes carrying different fluorophores and quenchers can be created very easily with the similar strategy used for the creation of DEC22-18 and DET22-18. Such DNA enzymes are useful in setting up various forms of multiplexed assays for the detection of important biological targets.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide chemistry and molecular biology, referred to but not explicitly described in this disclosure and examples are reported in the scientific literature and are well known to those skilled in the art.

Example 1

Oligonucleotides

Standard oligonucleotides were prepared by automated DNA synthesis using cyanoethylphosphoramidite chemistry (Keck Biotechnology Resource Laboratory, Yale University; Central Facility, McMaster University). Random-sequence DNA libraries were synthesized using an equimolar mixture of the four standard phosphoramidites. DNA oligonucleotides were purified by 10% preparative denaturing (8 M urea) polyacrylamide gel electrophoresis (PAGE) and their concentrations were determined spectroscopically and calculated using the Biopolymer Calculator program. (available at http://paris.chem.yale.edu)

Fluorescein and 4-(4-dimethylaminophenylazo)benzoic acid (DABCYL) labels were incorporated into the DNA during automated DNA synthesis using Fluorescein-dT amidite and DABCYL-dT amidite (Glen Research, Sterling, Va). The adenine ribonucleotide linkage was also introduced during solid-state synthesis using A-TOM-CE Phosphoramidite (Glen Research). Fluorescein and DABCYL modified oligonucleotides were purified by reverse phase liquid chromatography (HPLC) performed on a Beckman-Coulter HPLC System Gold with a 168 Diode Array detector. The HPLC column used was an Agilent Zorbax ODS C18 Column with dimensions of 4.6 mm_250 mm and a 5-micron bead diameter. Elution was achieved using a two-buffer system with buffer A being 0.1 M triethylammonium acetate (TEAA, pH 6.5) and buffer B being pure acetonitrile. The best separation results were achieved using a non-linear elution gradient (0% B for 5 min, 10% B to 30% B over 95 min) at a flow rate of 0.5 ml/min. The main peak was found to have very strong absorption at both 260 nm and 491 nm.

The TOM protective group on the 2_-hydroxyl group of the RNA linkage was removed by incubation with 150 _1 of 1M tetrabutylammonium fluoride (TBAF) in THF at 60° C. with shaking for 6 hr, followed by the addition of 250 _1 of 100 mM Tris (pH 8.3) and further incubation with shaking for 30 min at 37° C. The DNA was recovered using ethanol precipitation, dissolved in water containing 0.01% SDS, and the tetrabutylammonium salt was removed by centrifugation using a spin column (Nanosep 3K Omega, Pall Corp., Ann Arbor, Mich.).

Nucleoside 5_-triphosphates, [__ $^{32}$P]ATP and [__ $^{32}$P] dGTP were purchased from Amersham Pharmacia. Taq DNA polymerase, T4 DNA ligase and T4 polynucleotide kinase (PNK) were purchased from MBI Fermentas. All other chemical reagents were purchased from Sigma.

Example 2

Design of Oligonucleotides for Optimal Fluorescence-quenching

An RNA-cleavage based signaling DNA enzyme reporter that had a low background fluorescence in its inactive state under any given condition but could generate a large fluorescence signal upon cleavage of the single RNA linkage embedded in a DNA chain and flanked by a covalently linked fluorophore and quencher pair was created. This arrangement not only results in very efficient fluorescence-quenching because of the short distance between the fluorophore and the quencher, but also minimizes false positives because the quencher cannot be separated from the fluorophore until the RNA linkage is cleaved. To determine the optimal distance between the fluorophore and the quencher, a series of DNA oligonucleotides with the modifications as shown in FIG. 2A (F: fluorescein-dT; Q: DABCYL-dT; Ar: adenine ribonucleotide) were synthesized. The cleavage-dependent signaling behavior of these DNA molecules was assessed by treatment with 0.25M NaOH, and the data are shown in FIG. 2B, where $F_0$ and F are the fluorescence intensities of a relevant DNA solution measured immediately after the addition of 0.25 M NaOH (RNA cleavage yet to occur) and after an incubation for 20 hr (full RNA cleavage[19]). In this example, F1QDNA had the most significant fluorescence change (with an increase in intensity of ~70-fold), followed by F2QDNA (~30-fold). F3DNA produced a fluorescence enhancement of around 4-fold. The decrease in fluorescence enhancement with distance resulted from a higher value for $F_0$ as distance increased, owing to less efficient quenching. All FxQDNA systems (x=1-3) reached final intensity values that were similar to FDNA.

Example 3

Fluorescence Measurements

All measurements were made with 400 μl solutions on a Cary Eclipse Fluorescence Spectrophotometer (Varian). The excitation was set at 490 nm and emission at 520 nm.

Example 4

Kinetic Analyses

A typical reaction involved the following steps: (1) heat denaturation of DNA in water for 30 sec at 90 _C, (2) incubation for RNA cleavage at room temperature in a reaction buffer for a designated time, (3) addition of EDTA to 30 mM to stop the reaction, (4) separation of cleavage products by denaturing 10% PAGE, and (5) quantitation using a PhosphoImager and ImageQuant software. Aliquots of an RNA cleavage reaction solution were collected at different reaction time points that were all under 10% completion and the rate constant for the reaction was determined by plotting the natural logarithm of the fraction of DNA that remained unreacted vs. the reaction time. The negative slope of the line produced by a least-squares fit to the data was taken as the rate constant.

Example 5

Selection Scheme for the Isolation of a DNA Enzyme

Since F1QDNA had the largest fluorescence intensity increase, an RNA linkage immediately flanked by a fluorophore-containing nucleotide and a quencher-modified nucleotide was incorporated into the starting random-sequence pool to be used for the creation of DNA enzymes. A selection scheme to isolate signaling autocatalytic DNA molecules is shown in FIG. 3. The general scheme is shown in FIG. 3A and the specific sequences of a preferred embodiment are shown in FIG. 3B. In step I, a pool of single-stranded 86-nt DNA containing 43 random-sequence nucleotides is prepared. This is termed Library L1. In the sequence shown in FIG. 3B, $N_{43}$ denotes the random sequence of 43 nucleotides. 300 pmol of 5_-phosphorylated, gel-purified, 86-nt random-sequence DNA L1 was mixed in an equimolar ratio with template T1 and acceptor A1 (all sequences shown in FIG. 3B), heated to 90° C. for 30 sec, cooled to room temperature, and combined with 10_ligase buffer and T4 DNA ligase for DNA ligation to introduce the modified DNA domain. (Step I, FIG. 3A) The ligation mixture (50 _l) contained 50 mM Tris-HCl (pH 7.8 at 23° C.), 40 mM NaCl, 10 mM $MgCl_2$, 1 mg/ml BSA, 0.5 mM ATP, and 0.1 U (Weiss) $\_L^{-1}$ T4 DNA ligase. The solution was incubated at 23° C. for 1 hr and the ligated 109-nt DNA was purified by 10% denaturing PAGE. (Step II)

The 109-nt DNA population constructed as above was used as the initial pool (denoted generation 0 or G0), which was heated to 90° C. for 30 seconds, cooled to room temperature, and then combined with a 2_selection buffer (100 mM HEPES, pH 6.8 at 23° C., 800 mM NaCl, 200 mM KCl, 15 mM $MgCl_2$, 10 mM $MnCl_2$, 2.5 mM $CdCl_2$, 2 mM $CoCl_2$, 0.5 mM $NiCl_2$) to a final DNA concentration of 0.05 _M. (Step III) The mixture was incubated for self-cleavage at 23° C. for 5 hr.

The cleavage reaction was stopped by the addition of EDTA (pH 8.0) to a final concentration of 30 mM. The cleaved DNA was isolated by 10% denaturing PAGE. To increase the yield of DNA recovery and to track the status of 94-nt cleaved product, 0.25 pmol of strongly radioactive 94-nt DNA marker made by alkaline digestion of the 109-nt construct was used as the Acarrier DNA≅. The isolated cleavage product was amplified by PCR in 5_100 _1 reaction volume using primers P1 and P2 (FIG. 3B) (Step IV). The PCR reaction was monitored in real-time using SYBR Green (Molecular Probes). 2% of the amplified DNA product was used as the DNA template for a new PCR reaction in a 10_100 _1 reaction volume using primer P1 and ribo-terminated primer P3 (Step V). The reaction mixture also included 30 _Ci of [_-$^{32}$P]dGTP for DNA labeling.

The DNA product in the second PCR was recovered by ethanol precipitation, resuspended in 90 _L of 0.25 M NaOH and incubated at 90° C. for 10 min to cleave the single embedded RNA linkage. (Step VI) The cleavage solution was neutralized by adding 10 _L of 3 M Naiad (pH 5.2 at 23° C.) and ~86-nt single-stranded DNA fragment was isolated by denaturing 10% PAGE. The recovered DNA molecules were incubated with 10 units of PNK at 37° C. for 1 hr for DNA phosphorylation in a 100-_1 reaction mixture containing 50 mM Tris-HCl (pH 7.8 at 23° C.), 40 mM NaCl, 10 mM $MgCl_2$, 1 mg/ml BSA and 0.5 mM ATP. The reaction was stopped by the addition of EDTA to a final concentration of 30 mM. The 5$^1$-phosphorylated DNA was used for the second round of selection using the same procedure described for the first round of selection.

In this example, $Mg^{2+}$ and several divalent transition metal ions including $Mn^{2+}$, $Co^{2+}$, $Ni^{2+}$ and $Cd^{2+}$ were included in the selection buffer. The total concentration of divalent metal ions was chosen to be 15 mM with individual concentrations set at the following: 7.5 mM $Mg^{2+}$, 5 mM $Mn^{2+}$, 1.25 mM $Cd^{2+}$, 1 mM $Co^{2+}$, 0.25 mM $Ni^{2+}$. It is clearly apparent that other combinations and concentrations may also be effective.

Repeated rounds of selection lead to the selection of a highly efficient deoxyribozyme. The selection progress is summarized in FIG. 3C. None or low cleavage activity was observed for DNA sequences isolated in generations G0-G8. However, significant cleavage was seen in G9 and G10. By G11, more than 30% of the DNA construct was cleaved after a 5-hr incubation. The reaction time was then progressively reduced in order to derive very efficient DNA enzymes. The self-cleavage reaction was allowed to proceed for only 10 minutes in G12 and 1 minute in G13, and the reaction time was further reduced to 30 seconds in G14 and G15, to 5 seconds in G16 and G17, and finally to about 1 second in G18-G21. The DNA molecules in G22 were allowed to react for 1 minute and the cleaved DNA was cloned.

Example 6

Cloning and Sequencing of Selected Deoxyribozymes

DNA sequences from the 22nd round of selection were amplified by PCR and cloned into a vector by the TA cloning method. The plasmids containing individual catalysts were prepared using a Qiagen MiniPrep Kit. DNA sequencing was performed on an LCQ2000 capillary DNA sequencer (Beckman-Coulter) following the procedures recommended by the manufacturer.

Example 7

Isolation and Activity of an Autocalytic DNA Molecule

A single class of deoxyribozyme was found in the G22 pool after more than 20 clones were sequenced. The sequence of this autocatalytic DNA molecule, named DEC22-18, is given in FIG. 4A. The confirmation of its catalytic activity and the analysis of its metal ion requirements are shown FIG. 4B. The DNA enzyme was labeled at the phosphodiester bond linking the 23$^{rd}$ and 24$^{th}$ nucleotides with $^{32}$P. The uncleaved 109-nt DEC22-18 is therefore weakly fluorescent (since the Q moiety is still present) and highly radioactive. As shown in FIG. 4B upon self-cleavage, DEC22-18 gives rise to two cleavage products, with the 5=cleaved fragment (15-nt; P1) being strongly fluorescent but not radioactive and the 3=fragment (94-nt; P2) being only radioactive. The two cleavage products were obtained by the partial digestion of the deoxyribozyme with NaOH and used as the control (lane 1). When the deoxyribozyme was treated with water (lane 2), monovalent metal ions (lane 3), $Cd^{2+}$ (lane 5) or $Mg^{2+}$ (lane 8), no cleavage product was produced; when the DNA enzyme was treated with $Co^{2+}$ (lane 4), $Ni^{2+}$ (lane 6) or $Mn^{2+}$ (lane 7), it self-cleaved into the two expected DNA fragments with the matching signaling properties. In each case, the ratio of fluorescence intensity of P1 over that of uncleaved DEC22-18 was significantly larger than the ratio of radioactivity for these species, signifying a fluorescence enhancement consistent with the coupled catalysis-signaling mechanism. The data indicate that DEC22-18 is a metallo DNA enzyme capable of using Co(II), Ni(II) or Mn(II) as the divalent metal cofactor. Further experiments suggested that Co(II) is a preferred metal cofactor for DEC22-18.

Example 8

Determination of an Optimal Sequence

The optimal sequence for activity was determined using nucleotide truncation experiments. The truncation strategy is shown in FIG. 5. DEC22-18 exhibits a $k_{obs}$ of 1.0 $min^{-1}$ under the selection buffer conditions (50 mM HEPES, pH 6.8 at 23° C., 400 mM NaCl, 100 mM KCl, 7.5 mM $MgCl_2$, 5 mM $MnCl_2$, 1 mM $CoCl_2$, 0.25 mM $NiCl_2$, 1.25 mM $CdCl_2$). DEC22-18 is a large DNA molecule consisting of 109 nucleotides. To determine whether the DNA enzyme sequence could be minimized, a series of DNA molecules were synthesized with variable truncations from the 3'-end. These truncated mutants were examined for catalytic activity and the results are summarized in FIG. 5 (relative activities are shown with that of the wild-type DEC22-18 taken as 100). In one embodiment, the results indicate that the last 29 nucleotides of DEC22-18 can be deleted without significantly reducing the catalytic activity. In other embodiments, some truncated mutants are more effective than the wild-type molecule. In a preferred embodiment, the truncation of the last 26 nucleotides produced a 83-nt enzyme, denoted DEC22-18A, that had significantly improved catalytic activity with a $k_{obs}$ of 2.1 $min^{-1}$ under the selection buffer conditions. DEC22-18A is an even more effective catalyst when present in a solution containing 50 mM HEPES (pH 6.8 at 23° C.), 5 mM $MgCl_2$, 10 mM $CoCl_2$, without monovalent metal ions. In this case, the self-cleavage reaction was too fast to allow an accurate measurement of the rate constant using conventional manual quenching methods (data not shown). The $k_{obs}$ value can be estimated to be near 10 $min^{-1}$ based on the observation that nearly 50% of the DEC22-18A was cleaved in 3 seconds.

Example 9

Design of a Transacting DNA Enzyme

A trans acting DNA enzyme is provided. A secondary structure for DEC22-18A predicted by the M-fold program (http://bioinfo.math.rpi.edu/~mfold/dna) is shown in FIG. 6A. This structure was used to successfully design a trans-acting DNA enzyme system, DET22-18, by replacing the stem-1 and its loop existing in DEC22-18A with a stem made of eight base-pairs. This structure is shown in FIG. 6B. DET22-18 is a true DNA enzyme and a multiple-turnover DNA enzyme that cleaves substrate S1 according to Michaelis-Menten kinetics. FIG. 6C shows the data from a kinetic experiment where DET22-18 was used at 5 nM while the concentration of S1 was varied between 100-2000 nM. A $k_{cat}$ of 7.2_0.7 $min^{-1}$ and a $K_M$ of 0.94_$_{0.19}$_M were derived using GraFit software. These data indicate that the 58-nt DET22-18 is a very efficient DNA enzyme.

Example 10

Signaling Properties of DET22-18

The signaling behavior of the DET22-18/S1 substrate system was monitored in real time via fluorescence spectroscopy and the results are shown in FIG. 7. A less than optimal Co(II) concentration (1 mM rather than 10 mM) was used to slow down the cleavage reaction so that the fluorescence intensity changes could be monitored using the conventional spectroscopic method as well as to minimize any fluorescence quenching imposed by this metal ion. The signaling reaction was examined under two different enzyme: substrate ratios: (1) DET22-18 (E) in 10-fold excess over S1 (FIG. 7A) and (2) S1 in 10-fold excess over DET22-18 (FIG. 7B). In both cases, the system had a constant fluorescence intensity (first 10 minutes of the reaction) when S1 was incubated with metal ions alone without DET22-18. When the DNA enzyme was introduced, the fluorescence intensity of both solutions increased sharply. In FIG. 7A (E:S=10:1), the fluorescence enhancement (F/F0; F0 was the initial intensity and F was the intensity at any given time) increased at such a rapid rate that within 1 minute, 7.4-fold enhancement was observed (see inset graph). In FIG. 7B, the fluorescence enhancement increased at a reduced rate as expected because the concentration of the DNA enzyme was 10-fold less than that of the substrate. There was a 3.3-fold enhancement in 1-minute incubation (see inset graph), representing an initial turnover rate of 2.1/min (based on the observation that a 16-fold enhancement was observed when the reaction was completed). These data indicate that the signaling DNA enzyme can be used for signal generation under a broad range of substrate concentrations.

Example 11

Creation of a Signaling Allosteric DNA Enzyme

The stem-loop feature in the structure of DEC22-18A is ideal for the design of allosteric deoxyribozymes. To determine whether DEC22-18A could be easily designed into an allosteric DNA enzyme, an ATP aptamer was conjugated to the DNA enzyme through a weakened stem-1. This structure is shown in FIG. 8A. In the absence of ATP, the weak stem-1 does not associate strongly and as a result, the catalytic activity of this construct is fairly weak. However when ATP is introduced, the aptamer domain forms a stable complex with ATP to promote the formation of the stem-1 and thereby significantly increases the cleavage activity.

The conjugated DNA molecule or Aaptazyme≋ was assessed for signaling properties initially under the following reaction conditions: 50 mM HEPES (pH 6.8 at 23° C.), 14 mM $MgCl_2$, 1 mM $CoCl_2$, 23° C. The results are shown in FIG. 8A. The fluorescent intensity increased at a rate of ~0.04 fluorescence unit/min (f.u./min) when ATP was absent (first 5-minute incubation). Upon introduction of ATP (prior to the data recording at the 6th minute of the incubation), the signaling rate increased to ~0.16 f.u./minXa 4-fold enhancement in the catalytic rate. The system reached 80% of its maximal signaling capability in 3 minutes following the addition of ATP. The nature of the RNA-cleavage-dependent fluorescence signaling was confirmed by PAGE analysis of the cleavage products using a $^{32}P$-labeled DNA construct. An identical 4-fold activation of RNA cleavage by ATP was observed in the PAGE experiment.

The data shown in FIG. 8B suggests that the RNA cleavage activity of the aptamer-deoxyribozyme construct was high in the absence of ATP. This suggests that the enzymatic domain alone can form a sufficiently stable and active structure to render the efficient catalysis. To determine whether this ability of "self-folding" could be weakened at a higher temperature and a reduced $Co^{2+}$ concentration, a series of experiments at elevated temperatures and decreased $Co^{2+}$ concentrations were performed. FIG. 8C illustrates the results from a set of experiments conducted at 37° C. and 0.25 mM $Co^{2+}$ in the presence of 1 mM ATP (triangles) or 1 mM GTP (squares). Each reaction mixture was incubated in the absence of ATP or GTP for first 10 minutes, and ATP or GTP was introduced before data recording at the 11th minute of the reaction. In the absence of ATP and with or without GTP, the reaction proceeded at the same signaling rate (initial rate) of 9.5_$10^{-4}$ f.u./min. In the presence of ATP, the signaling rate increased to 1.8_$10^{-2}$ f.u./min, representing a nearly 20-fold of activation by ATP. The data in FIG. 8C also indicate that the target reporting was ATP-specific as GTP did not produce any significant signal enhancement. Signaling DNA enzymes with more responsive allosteric activation and less reduction in catalytic rate can be obtained through in vitro selection using partially randomized DEC22-18 sequences.

Those skilled in the art will readily recognize that modifications and equivalents of the specific embodiments disclosed herein can be achieved using no more than routine experimentation. Such modifications and equivalents are intended to be encompassed by the following claims.

REFERENCES (1). (a) Ellington, A. D.; Szostak, J. W. Nature 1990, 346, 818-822. (b) Tuerk, C.; Gold, L. Science 1990, 249, 505-510.

(2). (a) Famulok, M.; Mayer, G.; Blind, M. Acc. Chem. Res. 2001, 33, 591-599. (b) Wilson, D. S.; Szostak, J. W. Annu. Rev. Biochem. 1999; 68, 611-647.

(3). (a) Breaker, R. R. Nat. Biotechnol. 1997, 15, 427-431. (b) Breaker, R. R. Science 2000, 290, 2095-2096.

(4). (a) Sen D.; Geyer, C. R. Curr. Opin. Chem. Biol. 1998, 2, 680-687. (b) Li, Y.; Breaker, R. R. Curr. Opin. Struct. Biol. 1999, 9, 315-323. (c) Jaschke, A. Curr. Opin. Struct. Biol. 2001, 11, 321-326, (d) Emilsson, G. M.; Breaker, R. R. Cell Mol. Life Sci. 2002, 59, 596-607.

(5). (a) Breaker, R. R.; Joyce, G. F. Chem. Biol. 1994, 1, 223-229. (b) Cuenoud, B.; Szostak, J. W. Nature 1995; 375, 611-614. (c) Li, Y.; Sen, D. Nat. Struct. Biol. 1996, 3, 743-747. (d) Carmi, N.; Schultz, L. A.; Breaker, R. R. Chem. Biol. 1996, 3, 1039-1046. (e) Burmeister, J.; von Kiedrowski, G.; Ellington, A. D. Angew. Chem. Int. Ed. Engl. 1997, 36, 1321-1324. (f) Travascio, P.; Li, Y.; Sen, D. Chem. Biol. 1998, 5, 505-517. (g) Li, Y.; Breaker, R. R. Proc. Natl. Acad. Sci. U. S. A. 1999, 96, 2746-2751. (h) Li, Y.; Liu, Y.; Breaker, R. R. Biochemistry 2000, 39, 3106-3114. (i) Sheppard, T. L.; Ordoukhanian, P.; Joyce, G. F. Proc. Natl. Acad. Sci. USA 2000, 97, 7802-7807. (j) Levy, M.; Ellington, A. D. Bioorg. Med. Chem. 2001, 9 2581-2587.

(5). (a) Santoro, S. W.; Joyce, G. F. Proc. Nat. Acad. Sci. USA 1997, 94, 4262-6. (b) Li, J.; Zheng, W.; Kwon, A. H.; Lu, Y. Nucleic Acids Res. 2000, 28, 481-448, (c) Feldman, A. R.; Sen, D. J. Mol. Biol. 2001, 313, 283-294. (d) Wang, W.; Billen, L. P.; Li, Y. Chem. Biol. 2002, 9, 507-517.

(7). (a) 5a. (b) Santoro, S. W.; Joyce, G. F. Biochemistry 1998, 37, 13330-13342.

(8). 5d.

(9). Roth, A.; Breaker, R. R. Proc. Natl. Acad. Sci. U S A. 1998; 95, 6027-6031.

(10). (a) Santoro, S. W.; Joyce, G. F.; Sakthivel, K.; Gramatikova, S.; Barbas, C. F. J. Am. Chem. Soc. 2000, 122, 2433-2439. (b) Perrin, D. M.; Garestier, T.; Helene, C. J. Am. Chem. Soc. 2001, 123, 1556-1563. (c) Lermer, L.; Roupioz, Y.; Ting, R.; Perrin, D. M. J. Am. Chem. Soc. 2002, 124 9960-9961.

(11). Breaker, R. R. Curr. Opin. Biotech. 2002, 13, 31-39.

(12). (a) Soukup, G. A.; Breaker, R. R. Proc. Natl. Acad. Sci. USA. 1999, 96, 3584-3589. (b) Robertson, M. P.; Ellington, A. D. Nat. Biotechnol. 1999, 17, 62-66.

(13). (a) Wang, D. Y.; Sen, D. J. Mol. Biol. 2001, 310, 723-734. (b) Stojanovic, M. N.; de Prada, P.; Landry, D. W. ChemBioChem 2001, 2, 411-415. (c) Levy, M.; Ellington, A. D. Chem. Biol. 2002, 9, 417-426. (d) Stojanovic, M. N.; de Prada, P.; Landry, D. W. Nucleic Acids Res. 2000, 28, 2915-2918.

We claim:

1. A signaling DNA construct comprising the sequence of SEQ ID NO 10.

* * * * *

SEQUENCE LISTING

```
<160> NUMBER OF SEQ ID NOS: 15

<210> SEQ ID NO 1
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (16)..(16)
<223> OTHER INFORMATION: 16 = DABCYL dT quencher modified nucleotide
```

```
<220> FEATURE:
<221> NAME/KEY: misc_feature
<222> LOCATION: (17)..(18)
<223> OTHER INFORMATION: nucleotides 17 and 18 = g or t

<400> SEQUENCE: 12
gatgtgtccg tgcnnnnntt cga                                          23

<210> SEQ ID NO 2
<211> LENGTH: 86
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (10)..(52)
<223> OTHER INFORMATION: nucleotides 10 to 52 = a, c, g, or t

<400> SEQUENCE: 2
ttcttgatcn nnnnnnnnn nnnnnnnnnn nnnnnnnnnn nnnnnnnnnn nngcacggaa   60
ttcggtaagc ttggcacccg catcgt                                       86

<210> SEQ ID NO 3
<211> LENGTH: 33
<212> TYPE: DNA
<213> ORGANISM: Artificial Sequence
<220> FEATURE:
<223> OTHER INFORMATION: synthetic nucleotide sequence

<400> SEQUENCE: 3
ctacacaggc acgataccaa gctaagaact agc                               33

<210> SEQ ID NO 4
<211> LENGTH: 24
<212> TYPE: DNA
<213> ORGANISM: Artificial Sequence
<220> FEATURE:
<223> OTHER INFORMATION: synthetic nucleotide sequence

<400> SEQUENCE: 4
acgatgcggg tgccaagctt accg                                         24

<210> SEQ ID NO 5
<211> LENGTH: 32
<212> TYPE: DNA
<213> ORGANISM: Artificial Sequence
<220> FEATURE:
<223> OTHER INFORMATION: synthetic nucleotide sequence

<400> SEQUENCE: 5
ttacatctac gaatcaggtt cgattcttga tc                                32

<210> SEQ ID NO 6
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (23)..(23)
<223> OTHER INFORMATION: 23 = ribonucleotide A

<400> SEQUENCE: 6
ttacatctac gaatcaggtt cgn                                          23
```

```
<210> SEQ ID NO 7
<211> LENGTH: 109
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (16)..(16)
<223> OTHER INFORMATION: 16 = DABCYL dT quencher modified nucleotide

<400> SEQUENCE: 7
gatgtgtccg tgcnnnggtt cgattcttga tcgttgtcat tggcacacgg aggtttactg    60
agtggtaacc acgttgcatg gaattcggta agcttggcac ccgcatcgt              109

<210> SEQ ID NO 8
<211> LENGTH: 83
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (16)..(16)
<223> OTHER INFORMATION: 16 = DABCYL dT quencher modified nucleotide

<400> SEQUENCE: 8
gatgtgtccg tgcnnnggtt cgattcttga tcgttgtcat tggcacacgg aggtttactg    60
agtggtaacc acgttgcatg gaa                                            83

<210> SEQ ID NO 9
<211> LENGTH: 58
<212> TYPE: DNA
<213> ORGANISM: Artificial Sequence
<220> FEATURE:
<223> OTHER INFORMATION: synthetic nucleotide sequence

<400> SEQUENCE: 9
aagaatcgtt gtcattggca cacggaggtt tactgagtgg taaccacgtt gcatggaa      58

<210> SEQ ID NO 10
<211> LENGTH: 95
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
```

```
<222> LOCATION: (16)..(16)
<223> OTHER INFORMATION: 16 = DABCYL dT quencher modified nucleotide

<400> SEQUENCE: 10
gatgtgtccg tgcnnnggtt cgaggggggag tattgcggag gatagttgtc attggcacac    60
ggaggtttac tgagtggtaa ccacgttgca tggaa                                95

<210> SEQ ID NO 11
<211> LENGTH: 34
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (16)..(16)
<223> OTHER INFORMATION: 16 = DABCYL dT quencher modified nucleotide

<400> SEQUENCE: 11
gatgtgtccg tgcnnnggtt cgattcttgt gact                                 34

<210> SEQ ID NO 12
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide

<400> SEQUENCE: 12
gatgtgtccg tgcntttttt cga                                             23

<210> SEQ ID NO 13
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = DABCYL dT quencher modified nucleotide

<400> SEQUENCE: 13
gatgtgtccg tgcnntttttt cga                                            23

<210> SEQ ID NO 14
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
```

```
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (17)..(17)
<223> OTHER INFORMATION: 17 = DABCYL dT quencher modified nucleotide

<400> SEQUENCE: 14
gatgtgtccg tgcnntnttt cga                                            23

<210> SEQ ID NO 15
<211> LENGTH: 23
<212> TYPE: DNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (14)..(14)
<223> OTHER INFORMATION: 14 = fluorescein labelled dT nucleotide
<220> FEATURE:
<221> NAME/KEY: misc_feature
<222> LOCATION: (15)..(15)
<223> OTHER INFORMATION: 15 = ribonucleotide A
<220> FEATURE:
<221> NAME/KEY: misc_feature
<222> LOCATION: (18)..(18)
<223> OTHER INFORMATION: 18 = DABCYL dT quencher modified nucleotide

<400> SEQUENCE: 15
gatgtgtccg tgcnnttnttt cga                                           23
```